United States Patent [19]
Sevrain et al.

[11] Patent Number: 5,707,373
[45] Date of Patent: Jan. 13, 1998

[54] BONE FASTENER AND INSTRUMENT FOR INSERTION THEREOF

[75] Inventors: Lionel C. Sevrain, Val-de-la-Haye, France; Christophe J-P Sevrain, Ridgefield, Wash.

[73] Assignee: Ikonos Corporation, Portland, Oreg.

[21] Appl. No.: 635,410

[22] Filed: Apr. 26, 1996

Related U.S. Application Data

[60] Provisional application No. 60/011,647, Feb. 14, 1996.

[51] Int. Cl.⁶ ............................ A61B 17/86; A61B 17/88
[52] U.S. Cl. ........................... 606/72; 606/73; 606/104; 411/338
[58] Field of Search ........................ 606/72, 73, 104; 411/338, 339, 366, 173, 176, 177, 185, 187, 34, 38, 40, 43

[56] References Cited

U.S. PATENT DOCUMENTS

| | | | |
|---|---|---|---|
| 276,135 | 4/1883 | Cooley | 411/366 |
| 741,747 | 10/1903 | Walz | 411/139 |
| 1,510,416 | 9/1924 | Pietz et al. | 606/205 |
| 1,616,232 | 2/1927 | Roberts et al. | 411/338 |
| 2,489,870 | 11/1949 | Dzus | 606/73 |
| 3,019,887 | 2/1962 | Lowden | 198/711 |
| 3,281,171 | 10/1966 | Hughes | 403/280 |
| 3,875,936 | 4/1975 | Volz | 606/73 |
| 4,033,243 | 7/1977 | Kirrish et al. | 411/338 |
| 4,643,610 | 2/1987 | Bien | 403/407.1 |
| 4,651,724 | 3/1987 | Berentey et al. | 606/69 |
| 4,923,471 | 5/1990 | Morgan | 623/16 |
| 5,098,433 | 3/1992 | Freedland | 606/63 |
| 5,139,497 | 8/1992 | Tilghman et al. | 606/69 |
| 5,196,016 | 3/1993 | Buser et al. | 606/72 |
| 5,201,737 | 4/1993 | Leibinger et al. | 606/69 |
| 5,372,598 | 12/1994 | Luhr et al. | 606/69 |
| 5,433,719 | 7/1995 | Pennig | 606/73 |

OTHER PUBLICATIONS

Four pages from catalog of products offered by Codman & Shurtleff, undated, disclosing Burr Hole Buttons.

*Primary Examiner*—Michael Buiz
*Assistant Examiner*—David O. Reip
*Attorney, Agent, or Firm*—Klarquist Sparkman Campbell Leigh & Whinston, LLP

[57] ABSTRACT

A bone plate fastener for closing a craniotomy includes a cap and a base interconnected by a narrow cylindrical collar. The cap has an externally threaded stud that screws into an internally threaded bore of the collar, thereby allowing the cap and base to be brought into clamping engagement against the internal and external faces of a bone plate and surrounding bone. In a particularly disclosed embodiment, the base of the fastener is placed below a craniotomy hole with the collar projecting into the hole, and the stud of the cap is screwed into the bore of the base from above the hole to clamp a bone flap against the surrounding cranium. This device provides a method of quickly and securely replacing a bone cover into a craniotomy. The distance between the cap and base can be selected by how far the threaded stud of the cap is advanced into the internally threaded collar. The fastener is therefore adaptable for use in several regions of the skull having various thicknesses. An insertion tool with a long handle permits safe and convenient placement of the base between the brain and the internal face of the bone plate.

40 Claims, 7 Drawing Sheets

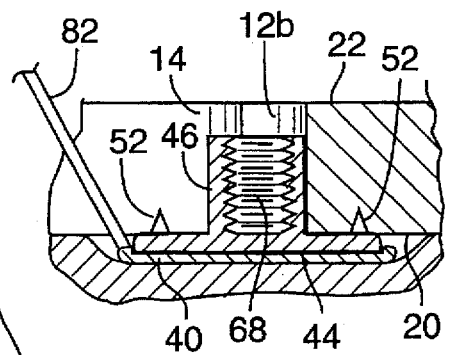
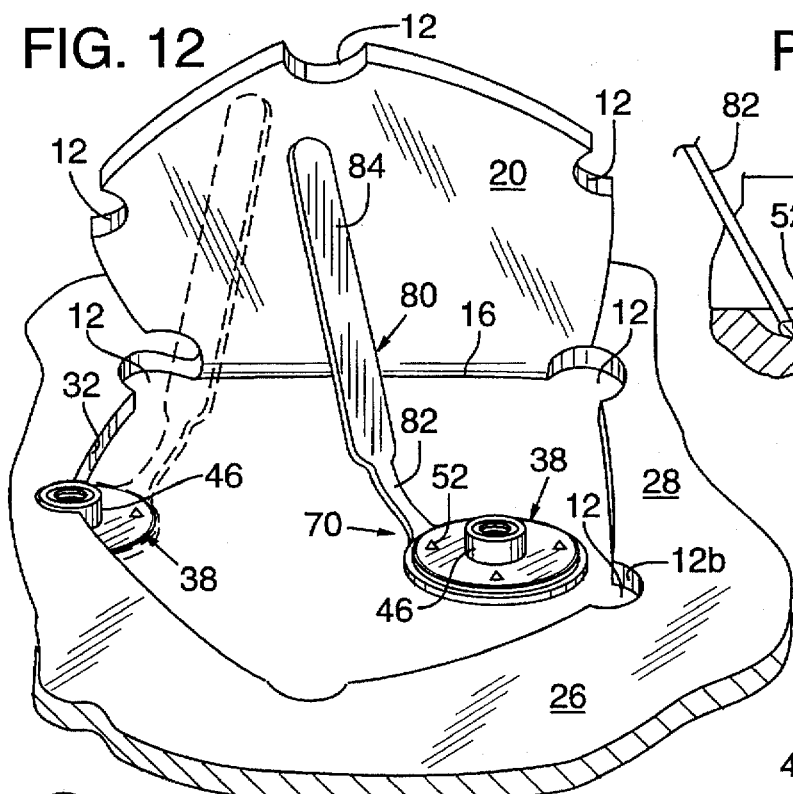
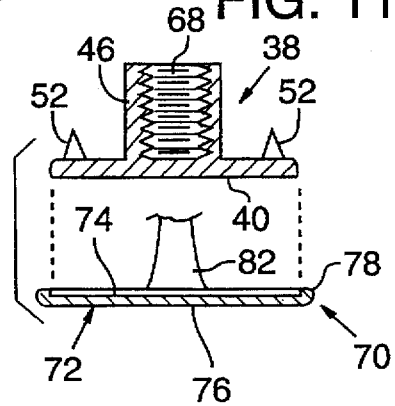
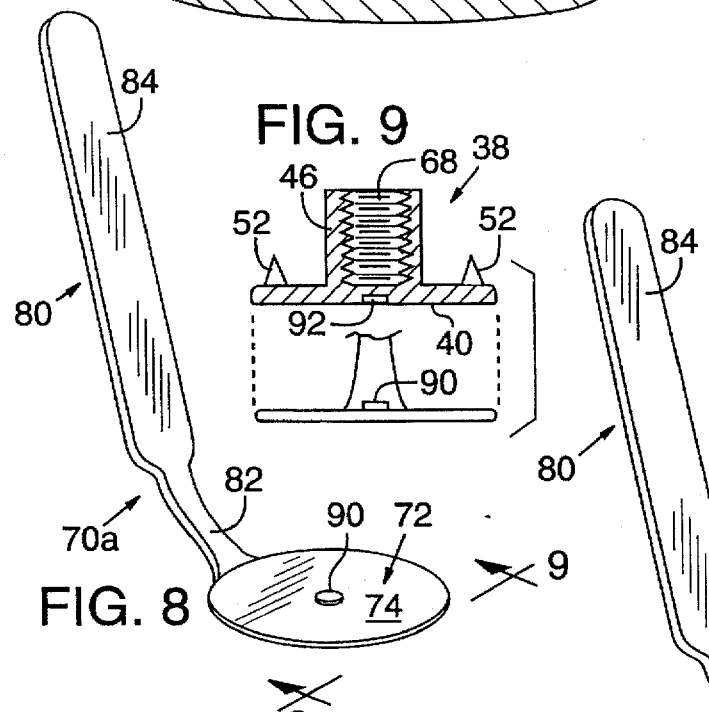
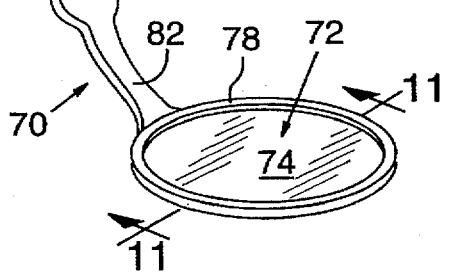

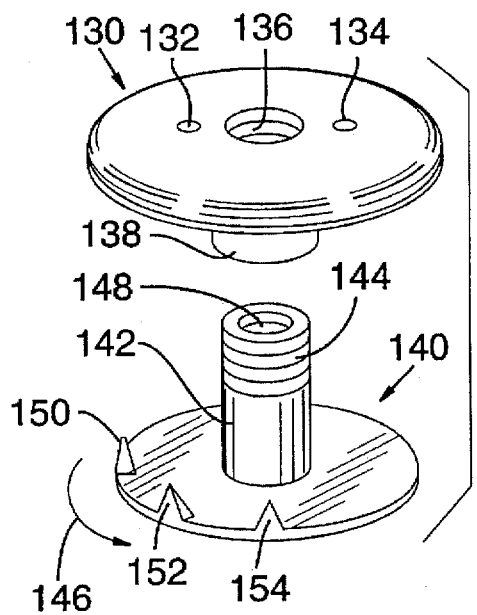
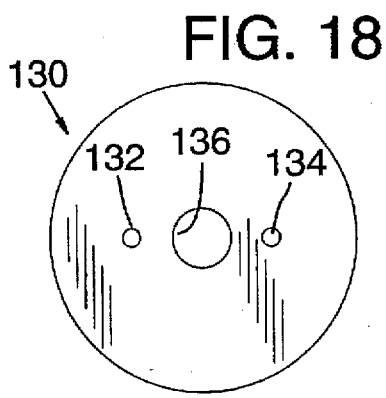
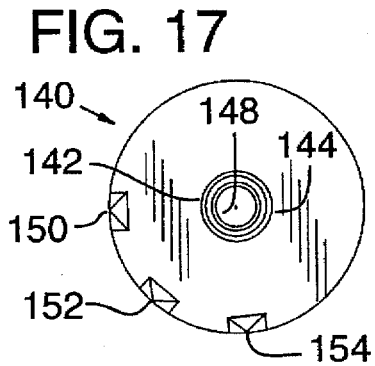
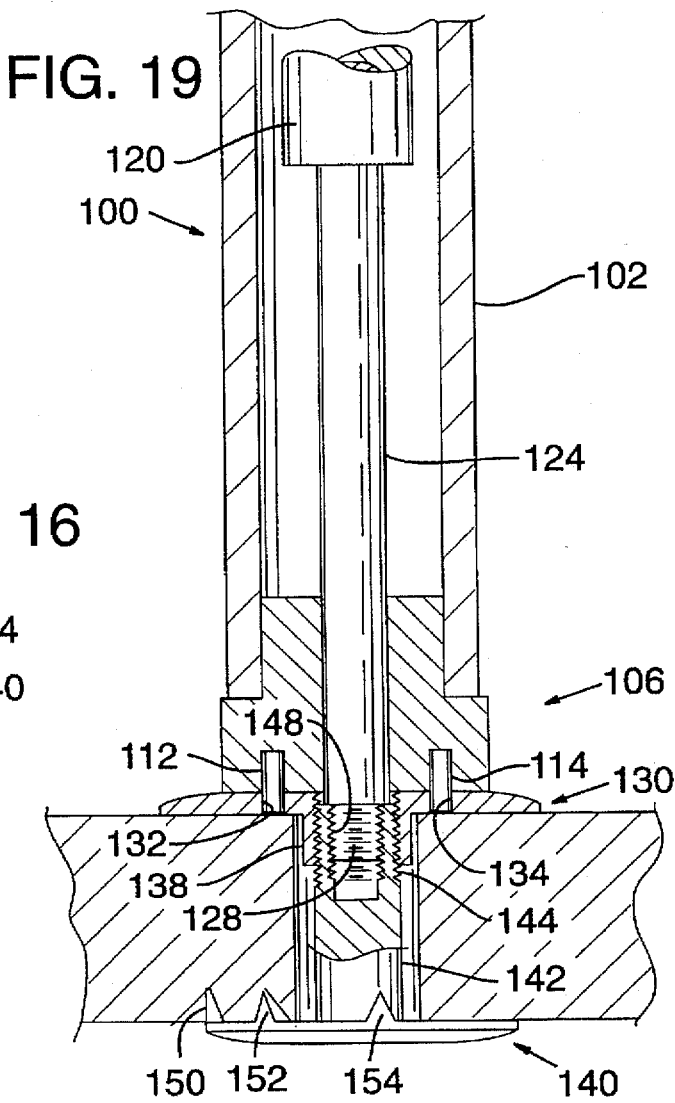
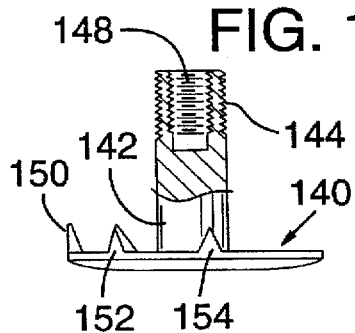

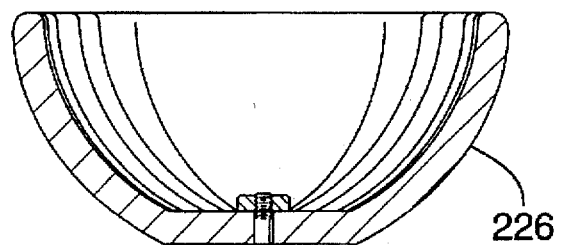
FIG. 24
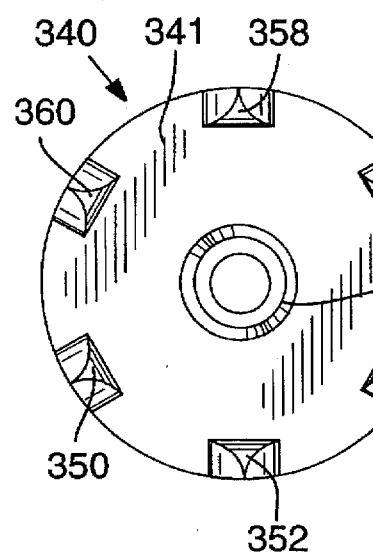
FIG. 25
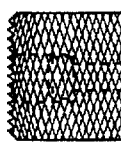
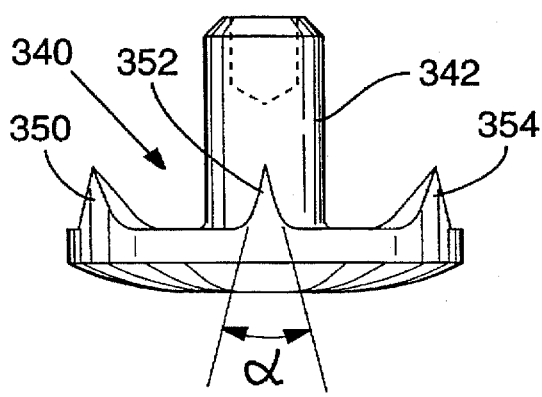
FIG. 26
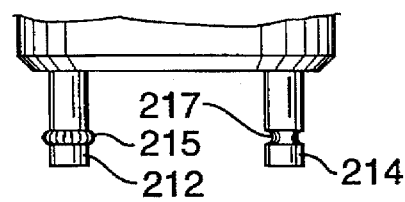
FIG. 24A

1

BONE FASTENER AND INSTRUMENT FOR INSERTION THEREOF

CROSS REFERENCE TO RELATED CASES

This case claims priority from provisional patent application Ser. No. 60/011,647 filed Feb. 14, 1996, and a provisional patent application entitled "Instrument For Engaging Threaded Members" that was filed on Mar. 25, 1996 under attorney docket no. 4902-44641, naming Lionel Sevrain as an inventor.

BACKGROUND OF THE INVENTION

1. Field of the Invention

This invention relates to a fastener for securing a bone plate to surrounding bone, for example when replacing a portion of the cranial vault removed during a craniotomy for a neurosurgical procedure. The invention also relates to an instrument for securing two threaded members to each other. The instrument may be used during neurosurgical procedures, or as a mechanical tool in many other contexts.

2. General Discussion of the Background

A craniotomy is a surgical procedure in which a portion of the cranial vault is removed or folded back in a flap to permit surgical access to the cranial contents (such as the brain). To perform the craniotomy, several burr holes are drilled through the skull. The number and position of these holes varies depending on the shape of bone to be removed. For example, three burr holes are drilled at corner points if a triangular bone flap is desired. The burr holes are then connected by osteotomy cuts, for example using a Gigli flexible saw which is passed internally between the burr holes. The saw is then oscillated back and forth to cut the skull along a line of separation (defined by the connecting osteotomies) connecting adjoining burr holes. The bone cover is subsequently lifted off the underlying dura mater to expose the brain. The bone cover may either be completely removed from the surgical site, or folded back in a flap along an uncut edge of the flap.

After completion of the operation, the bone cover must again be fixed in its original position to protect the underlying brain. Conventional craniotomy closure requires that holes be drilled in the bone plate and surrounding cranium along the osteotomy lines, and stainless steel wire or silk sutures are then passed through the holes to retain the plate in place. Unfortunately, drilling the holes is time consuming and potentially dangerous, because of the risk of introducing infection. The sutures are also unstable and prone to breakage. Suture instability or breakage can lead to dangerous movements of the cranial plate against the brain, with pathologic sequelae similar to a depressed skull fracture. The sutures closing the osteotomy lines are not aesthetically pleasing, because they can leave irregularities in the overlying surface of the face or scalp. This irregularity is particularly unsightly if the surface of the bone plate is not held substantially co-planar with the surrounding bone.

Various fixtures have previously been proposed for securing the bone cover to the surrounding cranium. U.S. Pat. No. 5,201,737 discloses a flexible plate having a plurality of vanes with holes for receiving bone screws. The plate is placed over a cranial burr hole and adjoining osteotomy lines to provide external fixation of the bone cover to the surrounding cranium.

Other external bone plates are shown in U.S. Pat. Nos. 4,651,724; 4,923,471; 5,139,497 and 5,372,498. All of these plates are designed for external application to fractured bones, and require placement of a plurality of screws through the plates. As with the plate in U.S. Pat. No. 5,201,737 discussed above, placement of multiple screws through the plates is time predisposes to catastrophic infection, and is difficult to remove once in place.

A variety of fixation devices are also known for fusing fractured bones. An example of such a device is U.S. Pat. No. 2,511,051, in which an externally threaded stud screws into an internally threaded shank. Movement of the stud into the shank is guided by an hexagonal wrench that is inserted through the shank into a countersunk receptacle on the tip of the threaded stud.

U.S. Pat. No. 3,875,936 shows an attachment for replacing a trochanteric head to the femur by providing a barbed shear washer between the femur and trochanteric head. U.S. Pat. No. 5,098,433 uses a winged compression bolt for fusing fractured bones. U.S. Pat. Nos. 5,196,016 and 5,433,719 discloses fixation pins or screws for retaining bone fragments against one another.

In spite of the use of a variety of fasteners in orthopedic and neurosurgical procedures, improved techniques are still being sought to secure a cranial cover to the surrounding cranium following a craniotomy. Improved methods and devices for securing the fasteners to the skull are also disclosed.

Accordingly, it is an object of the present invention to provide a fastener that is especially suitable for closure of craniotomies.

Yet another object is to provide such a fastener that can be quickly and efficiently installed, and which is capable of easy removal in the event that subsequent intracranial access is required for another neurosurgical procedure.

Yet another object of the invention is to provide such a fastener that avoids the aesthetic drawbacks of prior fasteners, such as large indentations in skin overlying the craniotomy.

It is another object of the invention to provide such a fastener, and an instrument for manipulating the fastener, that allows it to be easily inserted and removed, yet which provides a potentially permanent and fixation of the cranial cover, thereby avoiding the potentially catastrophic neurological consequences that can result from dislodgement or depression of the cranial cover.

Finally, it is an object of the invention to provide an instrument that is useful for engaging first and second members to each other, particularly when the engagement must occur on opposite surfaces, and one of the surfaces is not easily accessible.

SUMMARY OF THE INVENTION

These and other objects are achieved by the bone cover fastener of the present invention, which has first and second fastening members. An elongated, externally threaded stud projects from the first fastening member, while an elongated internally threaded collar projects from the second fastening member. The stud is rotationally threaded into the collar, with the collar extending between the fastening members. The collar fits through the burr hole of a craniotomy incision, and each fastening member is wider than the collar and the burr hole to provide clamping surfaces above and below the burr hole that engage the internal and external surfaces of the bone cover and surrounding cranium. Screwing the threaded stud into the internally threaded collar brings the opposing fastening members closer together, and tightens them against the internal and external surfaces of the bone cover and surrounding cranium. The fastening members overlap margins of the burr hole and adjoining osteotomy lines to securely fix the bone cover to the surrounding bone.

In a disclosed embodiment, one of the fastening members is a base which includes a disc having a flat inner face and a flat outer face. A plurality of raised barbs extend from the inner face of the base to provide frictional engagement between the disc and bone. The other fastening member is a cap with an outer face that may be flat or convex, and a recess is provided in the outer face for engaging a drive member that rotates the cap. An externally threaded stud projects from an inner face of the base and an internally threaded collar projects from an inner face of the cap. The stud is approximately as long as the collar. The stud may be screwed partially or entirely into the collar, depending on the thickness of the bone cover. Hence the fastener has the versatility to be used in different locations of the skull, where bone thickness varies.

The fastener is used in a method for fixing a bone plate, such as a cranial cover, in a bone defect, such as a craniotomy opening. The bone plate has opposing internal and external surfaces that are to be held in position substantially co-planar with internal and external surfaces of surrounding bone. The method provides the steps of placing the base and cap of the fastening member on opposing internal and external surfaces of the bone plate, with the collar projecting into the hole, and a portion of the base and a portion of the cap overlapping the border of the junction between the bone plate and surrounding bone. The base and cap are then rotated into threaded engagement with one another, until the cap and base tightly engage opposing surfaces of the bone plate and surrounding bone to clamp the bone plate in place. In particularly preferred embodiments, the fastener is placed through a craniotomy burr hole, with the cap and base covering and closing the burr hole.

In another embodiment, the base is positioned beneath the burr hole and against the internal surface of the bone plate by a positioning instrument. The instrument includes a disc-shaped platform, preferably having flat upper and lower faces. An upward projection from the base is designed to engage the fastener base and hold it in a desired position on the platform. The positioning instrument allows the base to be moved into a desired position against the internal surface of the bone plate, and pushed up against the bone plate to the barbs on the base into an internal face of the bone. The positioning instrument is particularly useful in neurosurgical procedures, because it allows the base to be positioned between the brain and skull while minimizing trauma to the brain.

In yet another embodiment of the invention, a fastening instrument is provided to secure first and second members to each other. The instrument includes a sleeve, a shaft or rod that slides within the sleeve, an attachment mechanism on the sleeve for engaging the first member to the instrument, and an engagement structure on the shaft that engages the second member and pulls it into engagement with the first member. In more particular embodiments, the sleeve includes a handle extending out from the sleeve, and the rod includes a handle that allows the rod to be rotated and reciprocated relative to the sleeve. There is a threaded tip on the rod that engages an internally threaded collar of the first member to screw the first and second member to be moved into engagement with each other.

In a more particular embodiment, the instrument includes a sleeve that has a handle (such as a rod or disc) extending from the sleeve. A rod slides within the sleeve, and has a threaded tip at a distal end of the rod, and a handle (such as a disc or curved hand grip) near a proximal end of the rod. The handle extends perpendicularly to the rod, and allows an operator to both rotate the rod and move the rod axially within the sleeve. A distal tip of the sleeve that surrounds the threaded rod has a plurality of locking members or prongs that extend from the tip of the sleeve and fit into complementary receptacles on one of the fasteners to lock the fastener to the tip of the sleeve, for example by frictional engagement of the prongs to one of the fasteners.

The instrument is designed to engage two threaded fasteners to each other. The fastener includes a cap and a base, and a receptacle in the cap that engages the prongs on the sleeve to lock the cap to the sleeve. The cap also includes an opening through which the rod can slide. The base of the fastener includes a post having both internal and internal threads, and the threaded tip of the rod has threads that are complementary to the internal threads of the post. The cap has a collar with internal threads that are complementary to the external threads on the post.

The fasteners are attached to each other by first engaging the fastener cap to the sleeve of the base by introducing the prongs into the receptacles on the cap. The rod is then extended through the cap, and the base secured to the rod by threading the threaded tip of the rod into the internally threaded post of the base. The sleeve is then axially advanced over the rod until the external threads of the base post abut the internal threads of the cap collar. The rod and sleeve are then rotated relative to each other (for example by rotating the shaft) to screw the externally threaded tip of the post on the base into the internally threaded collar of the cap. The threaded rod tip is then unscrewed from the internally threaded post of the base. The connected fasteners may then be disengaged from the instrument, for example by pulling the instrument away from the fasteners to disengage the locking member from the fasteners. Alternatively, axial movement of the rod towards the fasteners brings the threaded rod tip into abutment against the internal threads of the post, and pushes the fasteners off the locking members to disengage the fasteners from the instrument.

The instrument of the present invention can be used with many different types of fasteners, in many situations where two fasteners must be secured to each other in a difficult to reach location. The instrument is particularly useful when the fasteners are to be secured to opposite faces of a barrier that inhibits access to both faces of the barrier. One particular fastener with which the instrument can be used is the bone cover fastener of the present invention.

BRIEF DESCRIPTION OF THE DRAWINGS

FIG. 2 is an enlarged, perspective view of one of the fasteners of the present invention, wherein the cap and base are disengaged.

FIG. 7 is a cross-sectional view of the fastener showing placement of the fastener base with one embodiment of the positioning instrument.

FIG. 8 is a top perspective view of another embodiment of the positioning instrument.

FIG. 9 is a side elevational view, partially in cross-section, showing an alignment between a protuberance on the positioning instrument of FIG. 8, and an embodiment of the base that has an indentation into which the protuberance fits.

FIG. 10 is a top perspective view of the embodiment of the positioning instrument shown in FIG. 7, in which a peripheral flange extends upwardly from the platform.

FIG. 11 is a side elevational view of the positioning instrument shown in FIG. 10, partially in cross-section, demonstrating an alignment of the peripheral flange and fastener base.

FIG. 12 is a perspective view of a craniotomy opening in which a cranial bone flap has been folded back to expose the brain, and use of the positioning instrument is illustrated.

FIG. 15 is an enlarged, perspective view of another embodiment of the fasteners of the present invention, suitable for use with the fastening instrument, with the top and base disengaged.

FIG. 16 is a side elevational view of the base of the fastener of FIG. 15.

FIG. 17 is a top elevational view of the base of the fastener shown in FIG. 16.

FIG. 18 is a top elevational view of the cap of the fastener shown in FIG. 15.

FIG. 19 is a cross-sectional view through a craniotomy opening, showing the instrument of FIG. 13 engaging the cap and base of the fastener to one another.

FIGS. 24 and 24A are side elevational views showing another embodiment of the fastening instrument, in which the sleeve handle is a disc and the rod handle is a curved handgrip.

FIG. 25 is a top plan view of another embodiment of the base, showing distribution of the barbs around the inner face of the base.

FIG. 26 is a side elevational view of the base shown in FIG. 25, illustrating the profile of the barbs.

DETAILED DESCRIPTION OF A PREFERRED EMBODIMENT

Figure 1:
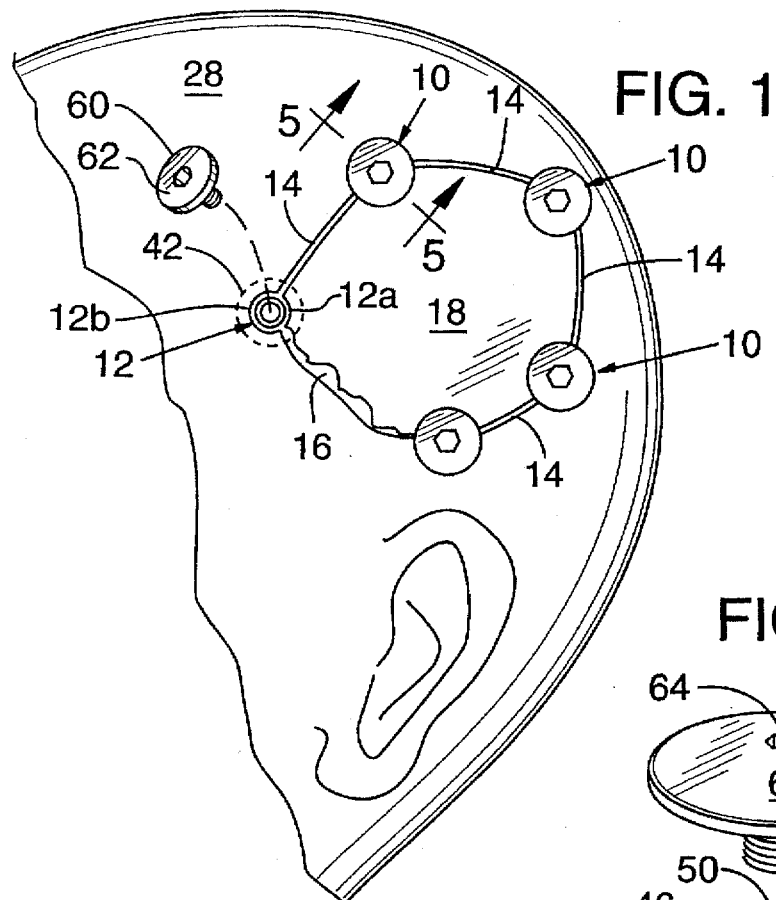
FIG. 1 is a schematic view of a portion of the human skull in which a craniotomy has been performed, and the fasteners of the present invention have been placed to secure the cranial cover to surrounding cranium.
Figure 3:
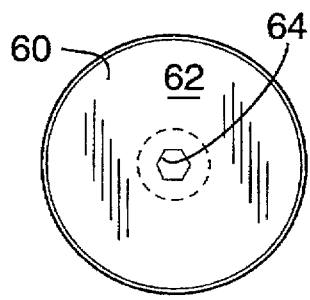
FIG. 3 is a top view of the cap of the fastener of FIG. 2.

The present invention includes fasteners for securing two table-like structure to each other. The invention also includes a positioning instrument that is particularly useful for positioning the fasteners in a surgical wound, and a fastening instrument for securing the fasteners to each other. This detailed description will describe several embodiments of the fasteners, as well as an instrument that can engage the fasteners to each other. The instrument can be used to secure many different types of fasteners to each other, but is shown in connection with the neurosurgical fasteners for purposes of illustration.

A clamp 10 is shown in the drawings for closing a craniotomy (FIG. 1), which is a particular type of table-like structure. As is known in the art, a craniotomy is performed by incising pericranium and muscle with cutting diathermy in the line of an intended bone flap. An incision is not made interiorly where a pedicle of pericranium or temporalis muscle is often left uncut to allow some blood supply to the bone and overlying tissue to remain intact. Alternatively, the pericranium and muscle may be detached completely from the intended bone flap.

The craniotomy is performed by making a series of burr holes 12 through the cranium about six or seven centimeters apart with a conventional trephine. The underlying dura mater is separated from the bone covering the osteotomy site ("the bone cover") using a periosteal elevator. Osteotomies 14 between the burr holes 12 are then made using a Gigli flexible saw that is passed between adjacent burr holes and moved back and forth to make the osteotomies from the internal to the external surfaces of the cranium. The base of the flap, as illustrated in FIG. 1, is not made with a saw. A bone forceps (such as a de Vilbis forceps) is used to cut between burr holes until the bridge breaks at base 16 when the flap is elevated.

After placement of the burr holes and performance of the osteotomies, a bone plate 18 is separated from the surrounding cranium along a line of separation formed by osteotomies 14. Each burr hole 12 has a plate portion 12a and a complementary cranial portion 12b which together form the completed hole 12. Trephines come in graduated sizes, for example between 0.5 and 2 inches (13–51 mm) diameter, for drilling burr holes of sizes varying across this usual range.

The bone plate 18 may be completely removed if osteotomies connect all of the burr holes 12. However, it is often preferred to leave an intact edge of the craniotomy (such as 16) to preserve the blood supply to the bone (as shown in FIG. 1). In either case, the bone plate or flap is referred to as the cranial cover.

Figure 5:
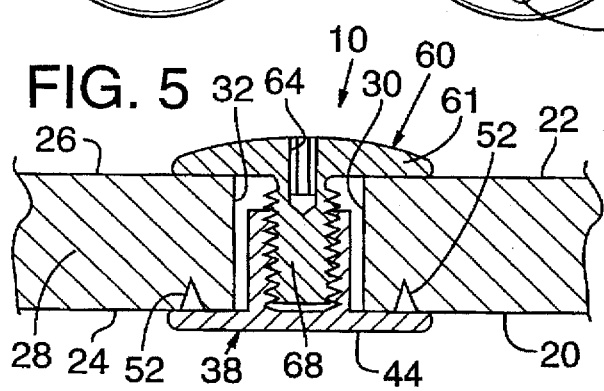
FIG. 5 is a cross-sectional view taken along section line 5—5 of FIG. 1.
Figure 13:
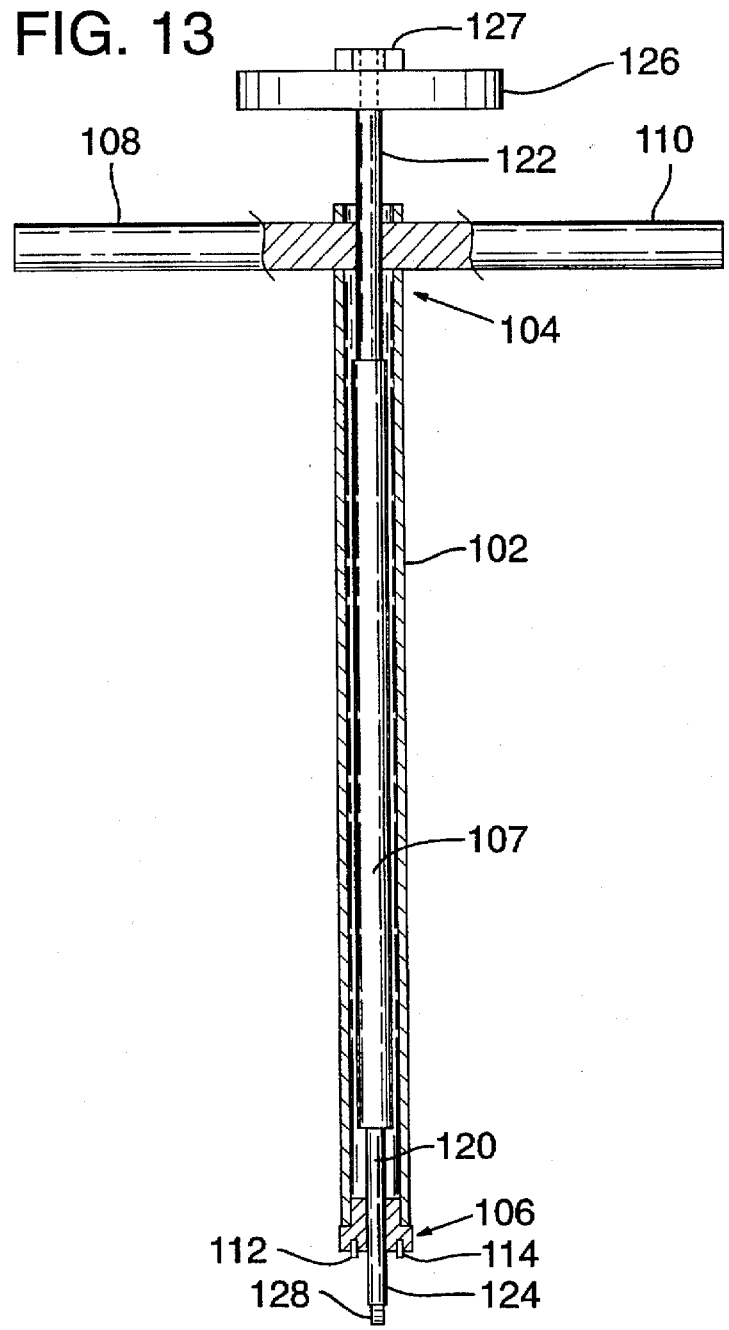
FIG. 13 is a cross-sectional view of a fastening instrument suitable for engaging another embodiment of the fasteners to one another.

After the neurosurgical procedure is performed, the bone defect must be repaired by placing the cranial cover 18 back in the defect with opposing internal surface 20 and external surface 22 (FIG. 5) substantially co-planar with the internal surface 24 and external surface 26 of surrounding cranium 28 (FIG. 5). A transverse face 30 of bone cover 18 must also be fixed in apposition with a transverse face 32 of cranium 28, along a border of junction defined by the osteotomy 14 between bone cover 18 and surrounding cranial bone 28.

Structure of the Fastner

In one embodiment, the fastener 10 includes a base 38 (FIGS. 2, 4–6) that includes a solid disc 40 having a flat inner face 42 and a flat outer face 44. Inner face 42 circumscribes an elongated, cylindrical collar 46 projecting outwardly from the center of inner face 42. An internally threaded bore 48 extends longitudinally through collar 46, but does not extend through disc 40. Hence bore 48 in this embodiment communicates only with a round opening 50 at the top of collar 46, and does not extend through disc 40, which has a flat, solid, lower face 44. In other embodiments, bore 48 may extend through the base.

Figure 4:
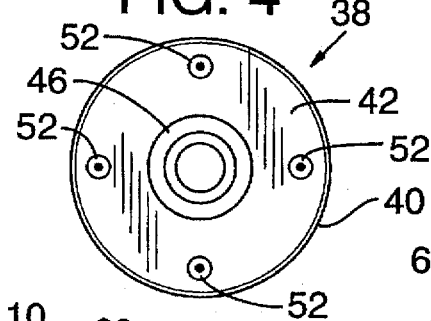
FIG. 4 is a top view of the base of the fastener of FIG. 2.
Figure 6:
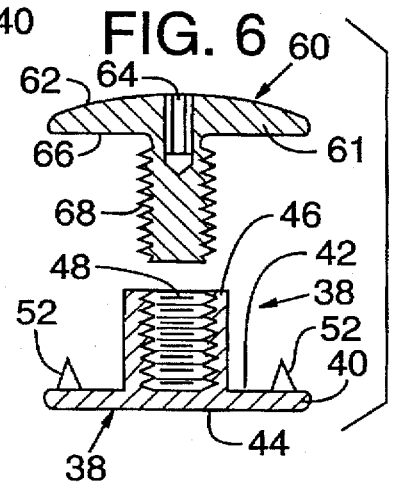
FIG. 6 is a cross-sectional view of the fastener shown in FIG. 2.

A plurality of raised, conical or pyramidal barbs 52 are integral with and extend upwardly from inner face 42 of disc 40. As best shown in FIG. 4, four barbs 52 are located on face 42, equally spaced around disc 40, and inwardly spaced from the perimeter of the disc. Barbs 52 taper to sharp tips 54 for engaging bone against which the barbs are placed, and into which the barbs may be embedded by pushing the barbs against the bone. The cancellous nature of the skull bone makes it particularly suitable for embedment of the barbs therein.

A cap 60 fastens to base 38 to form a fastener that secures bone cover 18 in place, and occludes the burr holes. Cap 60 is a solid disc 61 (FIGS. 5–6) with a convex outer face 62 that is smooth except for a recess 64 for engaging a complementary drive member (not shown) that rotates cap 60. The illustrated recess 64 is hexagonal, and designed to receive the tip of a surgical instrument resembling an Allen wrench. However, an elongated kerf could alternatively be scored in the surface 62 for receiving the tip of an instrument resembling a screw driver.

Cap 60 has a flat, annular inner face 66 from which an externally threaded stud 68 projects for inter-engagement with internally threaded bore 48 of collar 46. Stud 68 projects from the center of face 66, and the external threads are helical and machined to complement and screw into the internal helical threads of collar 46. Hence the collar resembles a nut into which the cap threads like a bolt. Stud 68 preferably has a length (extending perpendicularly away from face 66 along a longitudinal axis of fastener 10) that is approximately as long as threaded bore 48 of collar 46. The greatest width of cap 60 (as measured by the diameter of disc 61) and the greatest width of base 38 (as measured by the diameter of disc 40) are each wider than the outer diameter of cylindrical collar 46. The outer diameter of cylindrical collar 46 is less than the diameter of burr holes 12, but the diameters of discs 40 and 61 are greater than the diameter of burr holes 12. Cap 60 and base 38 each have a longitudinal axis of symmetry, such that the fastener when assembled is symmetric.

Method of Use to Close Craniotomy

The fastener 10 is used in a method of replacing a bone plate, such as cranial cover 18, following a craniotomy. As already described, the craniotomy is performed by providing a plurality of craniotomy holes, such as burr holes 12, through the skull. The burr holes are subsequently connected by osteotomies 14 to create a separation border for the cranial bone cover (which may be a plate that is removed or a flap that is folded back along one edge). The craniotomy opening therefore includes a portion 12a of burr hole 12 formed in cranial cover 18, and a complementary portion 12b of the hole formed in surrounding cranial bone 28.

Bone cover 18 has internal face 20 and external face 22 that are respectively placed in substantially co-planar relationship with internal face 24 and external face 26 of the surrounding cranial bone 28 when a craniotomy is closed. Opposing transverse faces 30, 32 of the bone cover and surrounding bone appose along the separation border when the bone cover is in place. Faces 30, 32 are substantially parallel to each other when in apposition.

In the method of the present invention, the bone cover 18 is folded back along a base 16, or completely removed as a plate, to expose the underlying dura mater and brain. Following the intracranial procedure, and prior to replacing the bone flap into its original orientation within the craniotomy opening, base 38 is placed below each burr hole 12 with the inner face 42 of base 38 against the internal surface 24 of cranium 28, such that one or more of barbs 52 engage the internal face 24. Base 38 overlaps the margins of hole 12 and the separation border between the cranial cover and surrounding bone (as shown in FIG. 1). Collar 46 projects upwardly into or through the portion 12b of the hole, but preferably does not extend out of the external surface. Cranial cover 18 is then replaced into the craniotomy opening, for example, by folding the bone flap along base 16 back down into the craniotomy opening.

Once cranial cover 18 is restored to its original position in the craniotomy opening, complementary portions 12a, 12b now reform hole 12. Collar 46 is centered in hole 12, with barbs 52 engaging the internal faces 20 and 24 of cover 18 and cranium 28 (FIG. 5). Cap 60 is then positioned over the reformed hole 12, with externally threaded stud 68 above opening 50. Stud 68 is introduced into collar 46 through opening 50, and a drive member (such as a surgical instrument resembling an Allen wrench) is inserted into hexagonal recess 64 to rotate cap 60 and advance stud 68 into threaded bore 48. Continued rotation of cap 60 diminishes the distance between base 38 and cap 60, to tighten inner faces 42, 66 of the base and cap against the internal and external surfaces of the cranium and cranial cover. The cap and base are thereby brought together in frictional engagement against opposing faces of the cranial cover 18 and surrounding bone 28, thereby clamping the cranial cover and surrounding bone to each other. Barbs 52 of base 38 anchor the base to both the cranial cover and surrounding bone, preventing rotation of the base while the cap is screwed into the collar. The base is attached to the bone as barbs 52 become progressively advanced into the bone by tightening of the fastener.

The fastener is used to clamp the cranial cover to the surrounding bone at one or more of the burr holes, and preferably all of the burr holes as shown in FIG. 1. A base 38 is therefore positioned below each burr hole 12 with collar 46 projecting up into the hole prior to replacement of cranial cover 18. A cap 60 is then screwed into each internally threaded collar until the cap and base clamp the bone cover 18 and surrounding cranium securely to each other. The cap and base are in a fixed relationship determined by the degree of advancement of the externally threaded stud 68 into the internally threaded collar 46, so that movement of the bone plate is substantially prevented. The bone plate and surrounding bone are held firmly in place with respect to each other, which avoids inadvertent depression of the cranial cover (with attendant catastrophic neurological consequences).

The smooth, convex top outer face 62 of cap 60 diminishes the aesthetic problem of visible indentations on the skull or face overlying the craniotomy burr holes. The closed base 44 tightly engages the internal surfaces of the cranial cover and surrounding cranium, providing ideal occlusion of the hole, to help avoid infection or trauma. The fastener also clamps the cranial cover in place quickly, thereby diminishing the period of time the brain must be exposed, and also reduces medical expenses associated with prolonged time in the operating room. The fastener is also easily removed, for example, by inserting an instrument into recess 64 of cap 60 and rotating the cap off of the fastener, to allow the bone flap to be subsequently removed if a follow-up neurosurgical procedure is required.

The fastener 10 is made of any biocompatible material, including stainless steel, titanium alloy, polyglycolic acid, silicone rubber, teflon or nylon. Titanium is a particularly preferred material. The biocompatibility of these and other materials can be enhanced by functionalization of the surface of the fasteners. Plasma gas discharge and corona treatment with reactive groups introduced on polymeric surfaces have been described as ways to modify biomaterial surfaces. See Lee et al., Biomaterials 12:443, 1991 and Lee et al., J. Colloid Interface Sci. 151:563, 1992.

The fastener 10 may be made in many different sizes. For purposes of illustration, the diameter of the stud 68 can be 7 mm (the same diameter as cylindrical bore 48); the external diameter of collar 46 may be 8 mm; the diameter of disc 61 can be 20 mm; the diameter of disc 40 may be 20 mm. In one preferred embodiment, stud 68 is 6 mm long, which is the same length as collar 46 and its internal bore 48.

The fastener of the present invention is adjustable for use in repairing craniotomies through bone of varying thickness. The pterion (in the temporo-parietal region) for example, is quite thin and may require a fastener with a 3 mm stud and collar, with advancement of the cap and base toward each other until the stud 68 has been completely advanced into collar 46 and face 66 of disc 61 abuts against collar 46. The 3 mm stud and collar, however, would also allow the fastener to clamp bones up to 6 mm thick (if the stud is only initially advanced into the collar). The parietal or frontal bone, however, may be 10–20 mm thick. A fastener with a 6 mm long stud 68 (and a 6 mm long internally threaded collar) can clamp bones together varying in thickness from 6 mm to 12 mm. A longer stud and collar (for example the stud and collar each 12 mm long) could clamp together bones from about 12 mm thick (when the fastener is fully tightened) to 24 mm thick (when the cap and base are initially engaged but before more rotation of the cap into the base occurs).

Other variations of the disclosed fastener are possible. The internally helically threaded collar, for example, may depend from the cap while the externally helically threaded stud may project from the base. The cap and base may assume many shapes other than circular, and may for example be square or triangular. Bone plates other than in the skull may be secured to surrounding bone, for example a relatively flat top bone such as the trapezium, mandible, maxilla, or bones of the orbit. The convex face of cap 60 may also be flat, particularly in areas of the skull (such as the temporal bone) with relatively flat external surfaces.

Positioning Instrument

Two embodiments of a positioning instrument 70 for use with the present invention are illustrated in FIGS. 7–12. In the first embodiment shown in FIGS. 7 and 10–12, the instrument includes a low profile disc-shaped platform 72 having a flat inner face 74 and a parallel flat outer face 76 (FIG. 11). The inner face 74 is surrounded by a continuous, circular peripheral flange 78 (FIGS. 10–11) that extends upwardly from the platform 72. An inner diameter of the peripheral flange 78 is about the same as an outer diameter of base 38 such that base 38 seats within flange 78. The peripheral flange inhibits transverse displacement of base 38 from platform 72.

An elongated handle 80 extends generally upwardly from platform 72 to enable the instrument to be grasped and manipulated. Handle 80 includes a first portion 82 that extends at about a forty-five degree angle from platform 72, and a second portion 84 that bends more toward a normal to the plane of platform 72, such that the angle between second portion 84 of handle 80 and a normal to platform 72 is about thirty degrees. This angled, substantially upright orientation of handle 80 increases the ease of manipulating the fastener base 38, and pulling base 38 upwardly against the internal face of the skull bone. In one preferred embodiment, platform 72 is about 1 mm thick, and the height of flange 78 above platform 72 is about 1 mm above inner face 74 of platform 72. The thickness of base disc 40 is 1–2 mm in this disclosed embodiment. Although many different dimensions can be used, these small dimensions are particularly useful in performing delicate neurosurgical procedures.

As illustrated in FIG. 11, the disc 40 of base 38 fits snugly on top face 74 of platform 72 within a 1 mm deep receptacle formed by peripheral flange 78, with the continuous peripheral edge of base 40 fitting tight against the peripheral edge of base disc 40. With the base in position on instrument 70, handle 80 is grasped by a surgeon (not shown) and moved to the craniotomy site (FIG. 12). The flat platform 72 of the instrument is then gently inserted between the cranium and underlying brain, to introduce the disc 40 between the brain and cranium 28. The fastener base is moved toward burr hole 12 until collar 46 is in place against surface 12b of the burr hole, with the flap 18 in the open position shown in FIG. 12. This procedure is then repeated until all of the desired number of fasteners are in place. Then bone flap 20 is returned to the position shown in FIG. 1, and caps 60 are screwed into the bases to secure the bone cover firmly in place.

Another embodiment of the positioning instrument is shown in FIGS. 8 and 9, wherein a cylindrical extension knob 90 is provided at the center of platform 72. A corresponding receptacle 92 of a size and shape similar to knob 90 is provided in the outer face of base disc 40. In one disclosed embodiment, the knob is about 1 mm high and 2 mm in diameter. The receptacle 92 is similarly 1 mm high and about 2 mm in diameter. The base 38 is placed on platform 74 of base 72, with knob 90 in receptacle 92 to inhibit transverse displacement of the base relative to the flat platform. The fastener bases are positioned below the burr hole, with the collar 46 extending through the hole, in the same manner as already described in connection with FIG. 12.

The receptacle 92 of FIGS. 8–9 is shown as an indentation in the outer face of base disc 40. However, in other embodiments, the receptacle can be continuous with internally threaded bore 68 through the collar.

Fastening Instrument

An instrument 100 for securing fastener members to each other is shown in FIGS. 13–22 to include an elongated tubular sleeve 102 (see especially FIG. 13) having a proximal end 104 (nearer the surgeon or other user) and a distal end 106 (father away from the surgeon or other user). Two tubular handle members 108, 110 extend diametrically away from each other, perpendicular to the axis of sleeve 102. Distal end 106 has two small posts 112, 114 (FIGS. 13, 14 and 19) projecting 1–3 mm (for example 2–3 mm) away from the flat surface 116 of distal end 106. Posts 112, 114 are spaced approximately 180° from each other, and serve as prongs that fasten the fastener to the instrument.

An elongated rod 120 (FIG. 13) slides within sleeve 102. A tubular guide member 107 may be placed in the sleeve 102 to fill empty space and inhibit relative transverse movement between the sleeve 102 and rod 120 that freely slides axially in the sleeve. Rod 120 includes a proximal end 122 and a distal end 124. A disc 126 is fixed to the proximal end 122 of rod 120 by hex nut 127, and extends perpendicularly to the longitudinal axis of rod 120. Disc 126 provides a handle on the instrument that can be grasped by a user to reciprocate or rotate rod 120 within sleeve 102.

The distal end 124 of rod 120 has an externally threaded, cylindrical, reduced diameter externally threaded tip 128. In one embodiment, sleeve 102 is approximately 14 cm long, with the span of arms 108, 110 being approximately 9 cm. Rod 120 is longer than sleeve 102, with a total length of approximately 16 mm from tip 128 to disc 126. The disc 126 is a solid, cylindrical disc having a diameter of approximately 3½ cm. Dimensions of the instrument may vary.

Instrument 100 is used to engage a first and second fastener to each other. In this disclosed embodiment, the first fastener is a cap 130, which is in the shape of a disc. Two openings 132, 134 through the disk are complementary to the size and location of posts 112, 114 on sleeve 102. Hence openings 132, 134 provide receptacles into which posts 112, 114 can be inserted and snugly received to secure or lock cap 130 to instrument 100, for example by frictional engagement between the posts 112, 114 and the receptacles in the cap 130.

A central opening 136 is provided through the center of the cap, along the axis of rotation of cap 130. Central opening 136 has a diameter only slightly greater than the diameter of rod 120, such that the rod can slide through and be guided by the walls of central opening 136. An internally threaded collar 138 (having helical internal threads) projects downwardly from cap 130 around central opening 136, and the central opening 136 communicates with and can extend through the collar 138.

The second fastener member is a base 140 which has the shape of a plate or disc with a central stud 142 projecting upwardly therefrom. Stud 142 is provided with external helical threads 144 that are complementary with the helical internal threads of collar 138, such that collar 138 can be rotated to thread cap 130 onto base 140.

Three sharp projections 150, 152, 154 extend upwardly from the disc of base 140 to help lock the base against a bearing surface. These projections 150–154 are located at the periphery of base 140, and are equally spaced about 60° from one another (such that all of the projections are on one-half of the base, preferably all within 120° of each other). The projections are substantially triangular, and each has a sharp apex that is suitable for embedment in a bearing surface (such as the internal surface of the skull).

Figure 20:
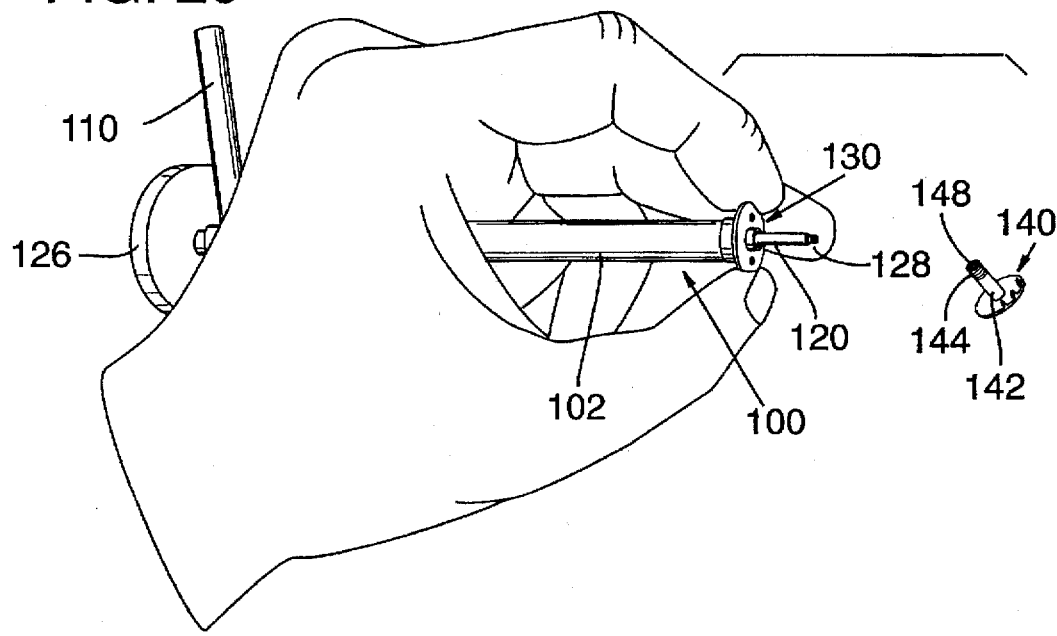
FIG. 20 is a view showing the fastener cap secured to the instrument.

Use of the instrument 100 to rotate the cap and base relative to one another, for engaging them to each other, is demonstrated in FIGS. 20–23. FIG. 20 shows the first step, in which rod 120 is inserted through opening 136 of cap 130 until locking posts 112, 114 are inserted into openings 132, 134 and cap 130 is secured in place on end 106 of sleeve 102. The frictional engagement between locking posts 112, 114 and the receptacles formed by openings 132, 134 holds cap 130 on end 106.

Figure 21:
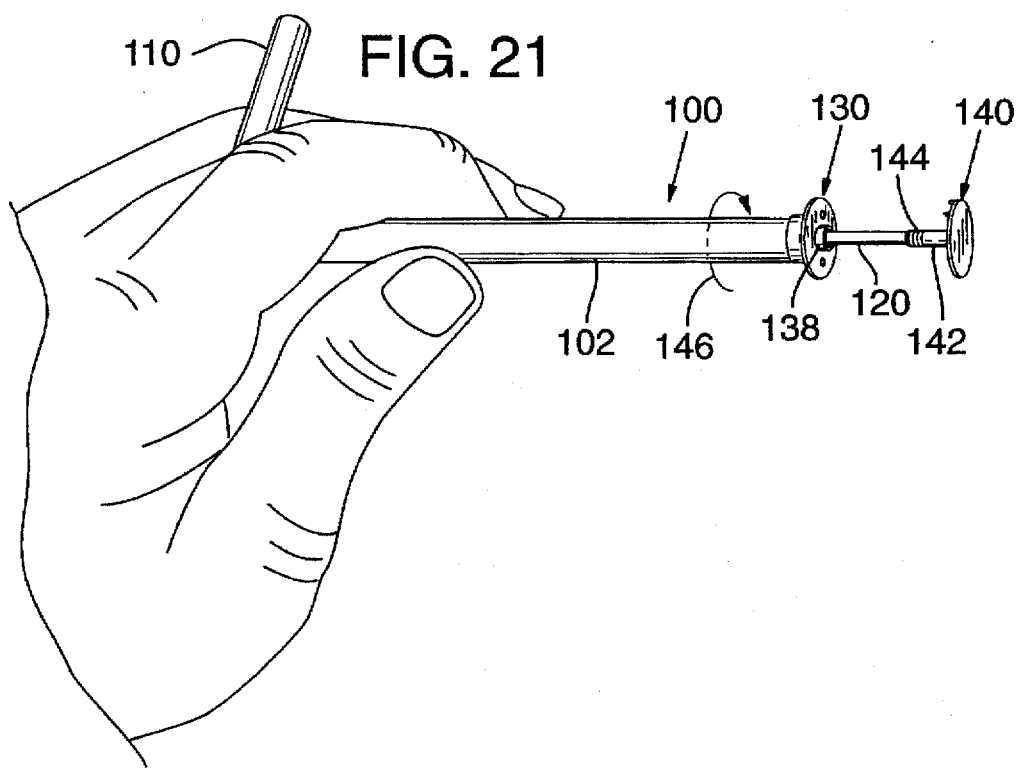
FIG. 21 is a view showing the fastener base secured to the instrument.

As shown in FIG. 21, base 140 is then attached to rod 120 by inserting threaded tip 128 (FIG. 20) into internally threaded stud 142 of base 140 (while the base is secured in place against an inner face of the bone plate). Rod 120 is then rotated in the direction of arrow 146 (FIG. 14 and 21) to screw threaded tip 128 into internally threaded stud 142 of the base. Rod 120 is rotated by turning disc 126 until base 140 is tightly secured on the tip. The step of threading base 140 onto tip 128 is preferably performed with rod 120 fully extended (as shown in FIG. 21) by exerting axial pressure against disc 126.

Figure 14:
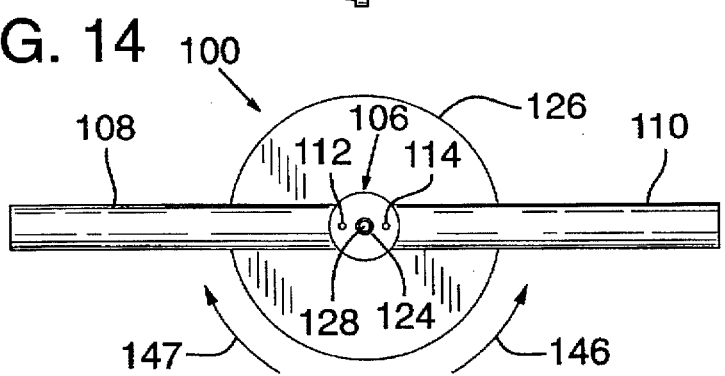
FIG. 14 is an end elevational view of the fastening instrument of FIG. 13.
Figure 22:
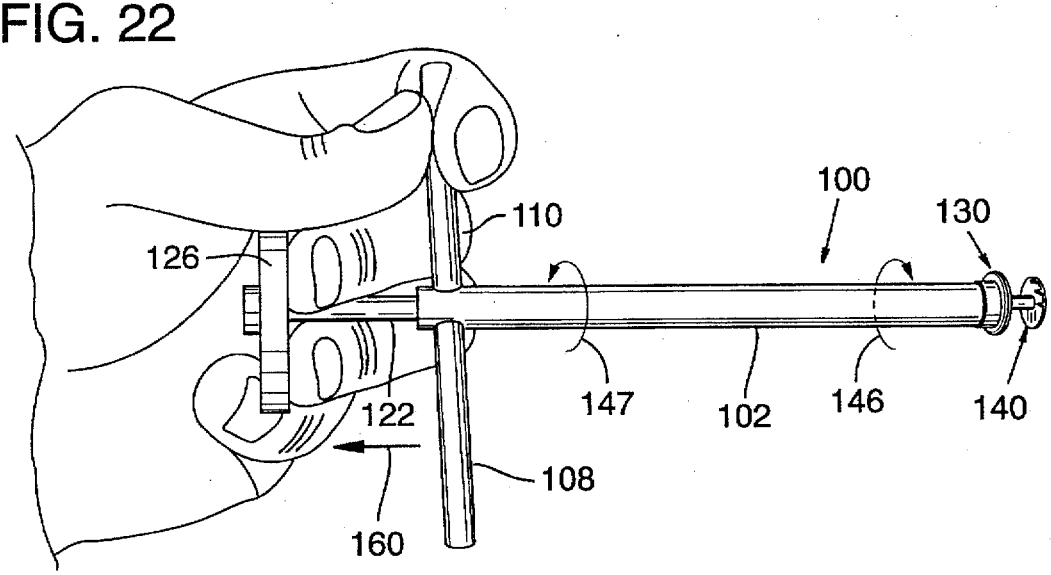
FIG. 22 is a view showing how the instrument is manipulated to rotate the fastener base relative to the fastener cap to secure the base and cap to each other.
Figure 23:
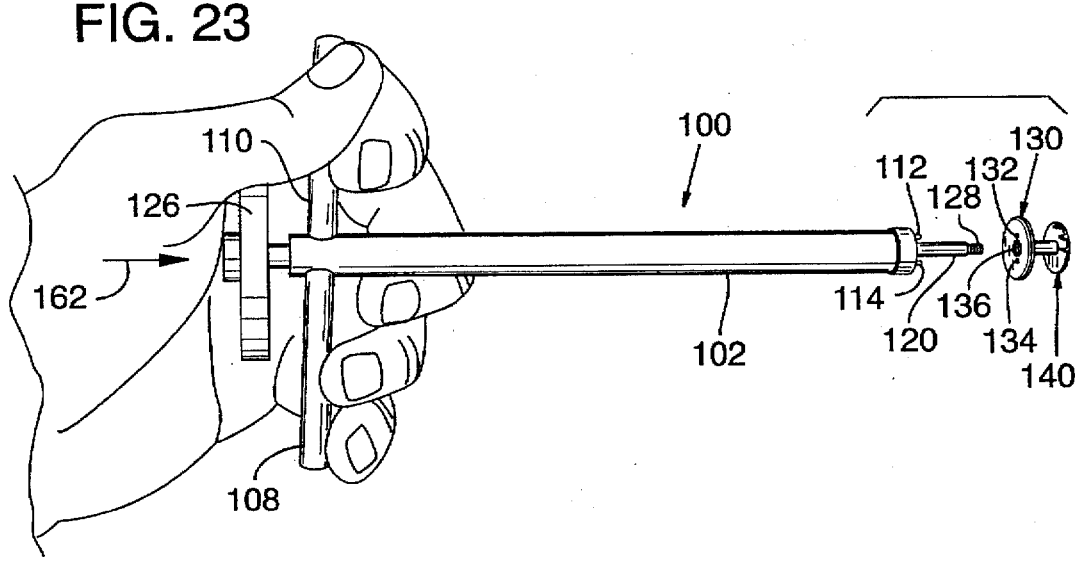
FIG. 23 is a view showing the instrument disengaged from the fastener.

Rod 120 is then axially retracted relative to sleeve 102 (or sleeve 102 is advanced relative to rod 120) (FIG. 22) to introduce external helical threads 144 on the stud 142 into the internal helical threads in 138 of cap 130. With the rod in the fully retracted position shown in FIG. 16, sleeve 102 is rotated by turning handle 110 in the rotational direction shown by arrow 146 (FIGS. 14 and 22). Base 140 will remain stationary, because barbed projections 150–154 on the base engage bone, and inhibit rotation of the base. Hence rotation of sleeve 102 in the direction shown by arrow 146 screws internally threaded collar 138 on to externally threaded stud 142.

After collar 138 has been fully screwed on to base 140, disc handle 126 is then rotated in the direction of arrow 147 (the opposite direction of arrow 146) to unscrew threaded tip 128 of the shaft 120 from the internal threads of stud 142. When tip 128 is fully unscrewed from stud 142 and collar 138, the tip is axially retracted from opening 136 to fully disengage the instrument 100 from the fastener. When used in a surgical procedure, the instrument may then be withdrawn from the surgical wound, leaving the fastener firmly in place engaging the opposing faces of the bone plate and surrounding bone.

The fastening instrument 100 can also be used in non-surgical applications, for example securing a fastener to opposing faces of a work piece such as a wall or adjacent pieces of wood. Variations of the method of using the instrument can also be used, in both surgical and non-surgical applications. For example, the base 140 can be rotated to screw it on to threaded tip 128 instead of rotating threaded tip 128 to screw it into the base. Only relative rotation between the base and sleeve is needed. Similarly, the base collar can be screwed into the cap collar by providing relative rotation between the cap and base, without necessarily rotating the cap by turning the sleeve 102. The rod can instead be rotated (in a direction 147) to screw the base into the cap by relative rotation between the base and cap.

The relationships of the various parts of the instrument to the fastener are shown in FIG. 19. The arrangement of the parts in that drawing corresponds to the instrument as shown in FIG. 22, wherein rod 120 has been axially retracted and cap 130 rotated relative to base 140 to attach the cap and base by threaded engagement of the helical threads. As illustrated in FIG. 19, base disc 140 has a lesser diameter than cap 130. In the disclosed embodiment, base disc 140 has a diameter of about 11 mm, while cap 130 has a diameter of about 13 mm. Stud 142 has a height of about 9 mm, while the height of collar 138 is about 4 mm. The smaller diameter of base disc 140 helps the base fit better against the interior face of the cranial vault, which has a steeper curvature than the curvature of the outer cranial cover.

The barbs 150, 152 and 154 are all within a 120° sector of base disc 140. This allows the barbs to be placed on the intact portion of the skull bone, without being embedded into the removable portion of the cranial cover. Hence the cranial cover can be removed when desired by disengaging the cap and base, without disengaging the barbs from the bone of the plate that is to be removed.

Alternative Embodiment of Fastener Instrument

Another embodiment of the fastener instrument is shown in FIGS. 24–26, and is designated instrument 200. This instrument is similar to instrument 100 shown in FIGS. 13–23, hence like parts have been given like reference numerals plus 100 to denote the similar parts, beginning with instrument 200. This embodiment differs, however, in that the rod handle 226 is not a disc, but is instead a handle grip with an arcuate frusto-hemispherical outer face. Alternatively, the handle 226 may be hemispherical or spherical in shape. The advantage of this shape is that it presents an arcuate side surface that can be easily grasped by the hand, with the fingers directed somewhat inwardly (toward the longitudinal axis of the instrument 200). Handle 226 provides a secure handgrip that is also easily rotated during use of the instrument.

The sleeve handle 210 also differs from the perpendicular rods 108, 110 that served as the sleeve handle in instrument 100. The sleeve handle is instead a disc that circumscribes the sleeve 202 and extends perpendicularly outwardly therefrom. The circumferential face 211 of disc 210 is serrated or otherwise roughened to increase frictional engagement between face 211 and the hand of a surgeon or other user of the instrument. Improved frictional engagement between the handle and hand is particularly helpful, for example, in surgical procedures during which blood or other body fluids may moisten the handle and make it slippery.

The friction engaging posts 212, 214 have also been elongated to 2–3 mm (for example 3 mm) to provide prongs that more securely hold the fastener cap on the instrument. The receptacle holes have been correspondingly elongated, and tightly engage the posts 212, 214 to selectively hold the instrument and fastener together. FIG. 24A also shows an alternative embodiment of the posts or prongs in which a circular coil spring or O-ring 215 (shown in place on post 212) is seated in an annular indentation (shown as 217) on each post. The coil spring is somewhat resilient, such that the spring is slightly compressed as posts 212, 214 are introduced into the receptacles of the cap. These compression springs provide improved engagement of the posts to the cap, such that the cap is even less likely to be dislodged from the instrument during use. Secure engagement of the cap to the instrument is important to allow the instrument to be manipulated, if desired, with one hand.

Another embodiment of the fastener base is shown in FIGS. 25 and 26. The base 340 is shown with six barbs 350, 352, 354, 356, 358 and 360 distributed equally around the periphery of and extending from the inner face 341 of base 340. The barbs have a sharp profile, for example the apex of the barb forms and angle $\alpha$ that is about 30 degrees or less (FIG. 26). Each barb extends 2–3 mm in height above the surface of inner face 341. This height has been found to allow the barbs to enter bone (such as a bone plate) to a depth that provides particularly superior engagement between the fastener base and bone plate. Distribution of the barbs around the base (instead of placing the barbs in only a sector of the base, for example a 60° or 120° sector) allows the barbs to engage the bone plate even if the base rotates slightly from its original position of placement.

The fastener and instrument of the present invention are preferably made of a metallic material that is suitable for sterile use in surgical procedures. Titanium or stainless steel are examples of such materials. The invention also includes a fastener, positioning instrument, and fastening instrument that has been sterilized, for example in an autoclave, or by irradiation (e.g. irradiation with ultraviolet radiation), or by chemical sterilization (e.g. with disinfectants or antimicrobials).

Having illustrated and described the principles of the invention in several preferred embodiments, it should be apparent to those skilled in the art that the invention can be modified in arrangement and detail without departing from such principles.

We claim:

1. A fastener that can be fixed through an opening between adjacent members, each member having a near face and a far face, the fastener comprising:

first and second fastening members;

a first connector on the first fastening member;

a second connector on the second fastening member for connecting with the first connector;

a positioning member on the first fastening member for interacting with a positioning instrument extending through the second fastening member to position the first fastening member in a fastening position on the far face so that the first and second connectors can be interconnected, and the positioning instrument can be removed from the first fastening member while leaving the first and second connectors interconnected; and wherein the second fastening member is a cap having an outer face with a recess for engaging a drive member that rotates the cap, and an inner face from which the second connecter projects.

2. The fastener of claim 1 wherein the positioning instrument comprises a threaded tip, and the first connector comprises a threaded collar for engaging the threaded tip of the positioning instrument, and the second fastening member includes an opening through which the threaded tip can extend to engage the threaded collar.

3. The fastener of claim 2, further comprising the positioning instrument wherein the positioning instrument comprises:

a sleeve, a shaft that slides within the sleeve, an attachment device on the instrument that fits into a recess on the second fastening member to secure the second fastening member to the positioning instrument; and the threaded tip is a threaded tip on the shaft.

4. The fastener of claim 3 wherein the first and second fastening members have opposing inner faces that face each other when the fastener is assembled in use, and a projection extends from the inner face of the first fastening member to inhibit rotation of the first fastening member relative to the adjacent members.

5. The fastener of claim 2 wherein the second connector comprises a threaded stud that engages the threaded collar.

6. The fastener of claim 5, wherein the first connector comprises an internally threaded collar, and the threaded stud of the second connector engages the threads of the internally threaded collar.

7. The fastener of claim 1, wherein the first and second fastening members are sterilized for use in surgery.

8. A fastener that can be fixed through an opening between adjacent members each member having a near face and a far face, the fastener comprising:

first and second fastening members;

a first connector on the first fastening member;

a second connector on the second fastening member for connecting with the first connector;

a positioning member on the first fastening member for interacting with a positioning instrument extending through the second fastening member to position the first fastening member in a fastening position on the far face so that the first and second connectors can be interconnected and the positioning instrument can be removed from the first fastening member while leaving the first and second connectors interconnected;

wherein the first fastening member is a base with an inner face, and a projection projects from the inner face of the base to engage the far face of at least one of the adjacent members to inhibit rotation of the base relative to the adjacent members.

9. A fastener that can be fixed through an opening between adjacent members, each member having a near face and a far face, the fastener comprising:

first and second fastening members;

a first connector on the first fastening member;

a second connector on the second fastening member for connecting with the first connector;

a positioning member on the first fastening member for interacting with a positioning instrument extending through the second fastening member to position the first fastening member in a fastening position on the far face so that the first and second connectors can be interconnected, and the positioning instrument can be removed from the first fastening member while leaving the first and second connectors interconnected;

the second fastening member comprises a cap having a convex outer face with a recess for engaging a drive member that rotates the cap, and a flat inner face, and the second connector comprises a threaded stud that projects from the inner face of the cap; and the first fastening member is a base with an inner face, and the first connector comprises a collar that projects from the inner face of the first fastening member, and a plurality of raised barbs project from the inner face of the base in a same direction that the collar projects from the base.

10. A fastener sustem that can be fixed through an opening between adjacent members, each adjacent member having a near face and a far face, the fastener system comprising:

first and second fastening members;

a first connector on the first fastening member;

a second connector on the second fastening member for connecting with the first connector;

a projection from the first fastening member for inhibiting rotation of the first fastening member relative to the adjacent members;

a positioning member on the first fastening member for interacting with a positioning instrument extending from the near face; and a positioning device, comprising a platform member with a projection that engages the positioning member to maintain the first fastening member in a substantially stationary position on the positioning device.

11. The fastener system of claim 10 wherein the upward projection comprises a flange.

12. The fastener system of claim 11 wherein the flange comprises a continuous peripheral flange.

13. The fastener system of claim 10 wherein the first fastening member includes a lower face having an indentation therein, and the upward projection fits into the indentation.

14. A fastener that can be fixed through an opening between adjacent members, each adjacent member having a near face and a far face, the fastener comprising;

first and second fastening members;

a first threaded connector projecting from the first fastening member;

a second threaded connector projecting from the second fastening member for engagement with the first threaded connector;

wherein the first threaded connector is both externally and internally threaded to engage the threads of both the second threaded connector and a threaded portion of a positioning instrument that extends through the second threaded connector.

15. The fastener of claim 14, wherein the second fastening member further comprises indentations in an external surface for receiving a prong from the positioning instrument.

16. A fastener, comprising:

a base having an inner face;

an externally threaded elongated stud projecting away from the inner face of the base, the elongated stud having an internally threaded bore at a free end of the stud, and a plurality of raised barbs on the inner face of the base around the stud; and a cap comprising a recess for engaging a fastener instrument and securing the cap to a drive member, and an inner face of the cap from which an internally threaded collar projects for inter-engagement with the externally threaded stud, and an opening through the cap and collar for the fastener instrument to communicate with the internally threaded bore of the stud when the fastener is assembled.

17. The fastener of claim 16, wherein the fastener is sterilized for implantation in the human body.

18. The fastener of claim 16, wherein the base plate and cap are at least twice as wide as the internally threaded collar extending from the cap, and the externally threaded shank extending from the base, and the internally threaded collar extending from the cap, are each about 3–12 mm long.

19. The fastener of claim 16, further comprising the fastener instrument for engaging the cap and base to each other, wherein the fastener instrument comprises:

a sleeve;

a shaft that slides within the sleeve;

an attachment device on the instrument that fits in the recess on the cap to secure the cap to the fastener instrument; and a threaded tip on the shaft dimensioned to fit through the opening in the cap, and screw into the internally threaded bore to secure the base to the fastener instrument.

20. A method of fixing a bone plate in a bony defect, wherein the bone plate has opposing internal and external surfaces that are to be held in position substantially co-planar with internal and external surfaces of surrounding bone, and a transverse face of the bone plate is to be fixed in apposition against a transverse face of the surrounding bone along a border of junction between the bone plate and surrounding bone, the method comprising the steps of:

providing a first fastening member with an elongated externally threaded stud projecting from the first fastening member, and a second fastening member with an elongated internally threaded collar for mating in threaded engagement with the threaded stud of the first fastening member; and placing the first and second fastening members on opposing internal and external surfaces of the bone plate, with a portion of each fastening member overlapping the border of junction, and rotating the stud into the collar to bring the fasteners into tight engagement against the opposing internal and external surfaces of the bone plate.

21. The method of claim 20 further comprising the step of providing a local enlargement in the border of junction through which the collar passes.

22. The method of claim 21 wherein the local enlargement is a hole wide enough to allow the collar to pass through the hole, and the first and second fastening members are wider than the hole.

23. The method of claim 20, further comprising the step of providing a tool with an attached handle, wherein the step of placing the first and second fastening members on opposing surfaces of the bone plate comprises positioning one of the first and second fastening members against the internal surface of the bone plate with the tool.

24. The method of claim 23 wherein the tool comprises a platform with an attached handle, and the step of positioning one of the fastening members against the internal surface of the bone plate comprises placing one of the fastening members on the platform and manipulating the tool to position the one of the fastening members into a desired position against the internal surface of the bone plate.

25. A method of replacing a cranial bone plate following a craniotomy, wherein the craniotomy has been performed by providing a plurality of craniotomy holes through the skull that are subsequently connected by saw lines along a separation border to remove the cranial bone plate, thereby leaving a portion of a hole in the bone plate and a corresponding portion of the hole in a surrounding cranial bone, and the bone plate has internal and external faces that are to be placed substantially co-planar with surrounding internal and external faces of the surrounding cranial bone, with opposing transverse faces of the bone plate and the surrounding bone in apposition along the separation border, and the method comprises the steps of:

providing a fastener having a first member with an externally threaded stud projecting therefrom, and a second member with an internally threaded collar projecting therefrom, wherein the first and second members are wider than the hole through the skull, the collar fits through the hole, and the combined length of the collar and shank is at least as great as the distance between the internal and external faces of the bone plate;

after removing the bone plate, placing one of the first or second members beneath the portion of the hole in the surrounding bone, overlapping the separation border;

replacing the bone plate with the corresponding portion of the hole complementing the portion of the hole in the surrounding bone to reform the hole, with the collar projecting into the hole;

placing the other of the first or second member over the reformed hole and the external face of the surrounding bone and the bone plate, overlapping the separation border; and rotating the stud into the collar until the first and second members are brought into frictional engagement with and clamp the bone plate and the surrounding bone to each other.

26. The method of claim 25 further comprising the step of providing a fastening instrument having a sleeve with a shaft that slides within the sleeve, wherein the shaft comprises an externally threaded tip, further wherein the stud comprises an internally threaded bore, and the step of rotating the stud into the collar comprises screwing the threaded tip of the shaft into the internally threaded bore of the stud, and then rotating the internally threaded collar by rotating the sleeve.

27. The method of claim 25, wherein the step of placing one of the first or second members beneath the portion of the hole comprises providing a tool comprising a platform with an attached handle, wherein the platform has a projection that engages the one of the first or second members, and the handle is used to manipulate the platform to position the one of the first or second members beneath the portion of the hole.

28. A method of replacing a cranial bone plate following a craniotomy, wherein the craniotomy has been performed by providing a plurality of craniotomy holes through the skull that are subsequently connected by an osteotomy along a separation border to remove the cranial bone plate, thereby leaving a portion of a hole in the bone plate and a complementary portion of the hole in a surrounding cranial bone, and the bone plate has internal and external faces that are to be placed substantially co-planar with internal and external faces of the surrounding cranial bone to close the craniotomy, with opposing transverse faces of the bone plate and the surrounding bone in apposition along the separation border, and the method comprises the steps of:

providing a base comprising a disc having an inner face and an outer face, the inner face of the base circumscribing an elongated, externally threaded stud projecting from the inner face, and the base further comprises a plurality of raised barbs on the inner face of the base surrounding the collar;

providing a cap having an outer face that includes a recess, and an inner face from which an internally threaded collar projects for inter-engagement with the externally threaded stud, and an opening through the cap that communicates with the internally threaded collar, wherein the stud includes an internally threaded bore, the base and cap are each wider than the hole, the collar fits through the hole, and the base and cap are made of a biocompatible material suitable for implantation in the human body;

after removing the bone plate, placing the inner face of the base against the internal face of the surrounding bone, beneath the portion of the hole in the surrounding bone, overlapping the separation border, with the barbs engaging the internal face of the surrounding bone and the collar projecting through the portion of the hole in the surrounding bone;

replacing the bone plate with the complementary portion of the hole in the bone plate complementing the portion of the hole in the surrounding bone to reform the hole;

placing the cap over the reformed hole and against the external face of the surrounding bone and the bone plate, overlapping the separation border; and providing a fastener instrument comprising a sleeve, a shaft that slides within the sleeve wherein the shaft has a threaded tip, and a prong on the sleeve that fits within the receptacle on the cap to secure the sleeve to the cap;

inserting the prong into the recess in the cap to secure the sleeve to the cap;

inserting the threaded tip of the shaft through the opening through the cap and into the internally threaded bore in the shaft, then rotating the threaded tip to screw the threaded tip into the internally threaded bore of the stud;

rotating the shaft to screw the internally threaded collar of the cap onto the externally threaded stud to bring the cap and base together into frictional engagement, clamping the bone plate and the surrounding bone to each other;

rotating the shaft to unscrew the threaded tip from the internally threaded bore of the stud.

29. The method of claim 28 further comprising the step of subsequently removing the bone plate by screwing the threaded tip into the internally threaded bore, inserting the prong into the recess in the cap, and rotating the shaft to unscrew the collar from the stud.

30. An instrument for engaging first and second members to each other, comprising:

a sleeve;

a shaft that slides within the sleeve;

an attachment member on the instrument for engaging the first member to the instrument; and an engagement structure on the shaft that engages the second member and pulls it into engagement with the first member.

31. The instrument of claim 30, wherein the attachment member is an extension on a tip of the sleeve that fits into a receptacle in the first member, and the engagement structure is a threaded tip on the shaft that engages threads on the second member.

32. The instrument of claim 31 wherein the second member includes both internal and external threads, and the threaded tip engages either the internal or external threads, and the first member includes threads that engage a one of the internal or external threads that the threaded tip does not engage.

33. The instrument of claim 32, further comprising a fastener that includes a cap and a base, and a receptacle in the cap that receives the projection from the sleeve to lock the cap to the sleeve, further wherein the cap includes an opening though which the rod can slide.

34. The instrument of claim 33, wherein the base includes a post having internal threads and external threads, and the threaded tip of the rod has threads that are complementary with the internal threads of the post, and the cap has a collar with internal threads that are complementary with the external threads on the post.

35. The instrument of claim 30, wherein the first member includes a hole through which the threaded tip of the shaft can slide.

36. An instrument, comprising:

a sleeve that includes a handle extending from the sleeve;

a rod that slides within the sleeve;

a threaded tip on a first end of the rod; and a handle on a second end of the rod.

37. The instrument of claim 36, further comprising a projection from the sleeve configured to engage a member to be manipulated by the instrument.

38. The instrument of claim 36, wherein the handle on the rod comprises a curved hand grip.

39. The instrument of claim 36, wherein the handle extending from the sleeve extends perpendicularly from the sleeve.

40. A device, comprising: an elongated tubular sleeve with a proximal end and a distal end, wherein a handle member extends away from the proximal end of the sleeve, and the distal end includes a plurality of projections;

an elongated rod that slides within the sleeve, wherein the rod includes a proximal end and a distal end, a handle member attached on the proximal end of the rod, and an externally threaded tip at the distal end of the rod;

a first fastener member having indentations therein for tightly receiving the plurality of projections and securing the first fastener member to the sleeve, and an opening through the first fastener member through which the rod can slide when the first fastener member is secured to the sleeve, wherein the opening is internally threaded; and a second fastener member having sharp projections directed toward the first fastener member, and a projection from the second fastener member with internal threads that are complementary to the externally threaded tip of the rod, and external threads that are complementary to the internally threaded opening through the first fastener member.

* * * * *